United States Patent [19]
Dunshee et al.

[11] 4,346,700
[45] Aug. 31, 1982

[54] PRESSURE-SENSITIVE ADHESIVE SHEET MATERIAL

[75] Inventors: Wayne K. Dunshee, Maplewood; Janice B. Odegaard, Afton, both of Minn.

[73] Assignee: Minnesota Mining & Manufacturing Company, St. Paul, Minn.

[21] Appl. No.: 273,973

[22] Filed: Jun. 15, 1981

Related U.S. Application Data

[63] Continuation of Ser. No. 94,850, Nov. 16, 1979, abandoned, which is a continuation-in-part of Ser. No. 886,059, Mar. 13, 1978, abandoned.

[51] Int. Cl.³ .............................................. A61F 13/00
[52] U.S. Cl. ................................. 128/155; 128/132 D
[58] Field of Search ................... 128/155, 156, 132 R, 128/132 D; 428/343, 349; 260/42.41, 32.6 PQ, 42.32

[56] References Cited
U.S. PATENT DOCUMENTS

| | | | |
|---|---|---|---|
| 3,085,024 | 4/1963 | Blackford | 117/4 |
| 3,262,827 | 7/1966 | Kallander et al. | 428/343 |
| 3,434,472 | 3/1969 | Herniman | 428/343 |
| 3,816,347 | 6/1974 | Luh | 260/42.41 |

OTHER PUBLICATIONS
"Formulation and Behavior of . . . Chlorinated PE", Dow Chemical, Young, May 1972.

Primary Examiner—Kyle L. Howell
Assistant Examiner—T. J. Wallen
Attorney, Agent, or Firm—Cruzan Alexander; Donald M. Sell; Gary L. Griswold

[57] ABSTRACT

Pressure-sensitive adhesive sheet materials such as tapes and surgical drapes that are skin and joint conformable and comprise a backing consisting essentially of chlorinated polyethylene and a pressure-sensitive adhesive on at least a portion of a surface thereof.

8 Claims, 2 Drawing Figures

PRESSURE-SENSITIVE ADHESIVE SHEET MATERIAL

This application is a continuation of U.S. patent application Ser. No. 94,850 filed Nov. 16, 1979, now abandoned, which is, in turn, a continuation-in-part of U.S. patent application Ser. No. 886,059 filed March 13, 1978, now abandoned.

This invention relates to conformable pressure-sensitive adhesive sheet material such as tapes and surgical drapes. More specifically, this invention relates to conformable pressure-sensitive adhesive sheet materials having backings consisting essentially of chlorinated polyethylene.

Surgical drapes are positioned on the skin area over the portion of the anatomy which is the subject of the operation to insure the sterility of the site. Medical and surgical tapes and dressings are used to protect injured portions of the anatomy during the healing process. The tapes and dressings are used primarily to protect the injured portion from dirt, bacteria and other environmental contaminants. Ideally these protective devices should perform this primary function without further aggravating the injury or interfering with the healing process and with a minimum of additional pain and inconvenience.

To minimize the negative effects that can result from the use of adhesive tapes or drapes, it is desirable that they exhibit conformability and extensibility which is similar to skin. Skin is a very extensible material which stretches 20% to 30% during normal activities and up to 50% if needed. Skin is also resilient, which allows it to return to an unstretched condition when stress is removed. This property of skin does not meet the normal definition of elasticity such as found in the definition of an elastomer given by the American Society of Test Materials, ASTM, as a material which at room temperature can be repeatedly stretched to at least twice its original length and upon release of the stress will immediately return with force to its approximate original length. Skin does not snap back to its original length with force; instead it relaxes or draws itself back to its original length.

Tapes applied to the skin must stay exactly in place without shifting relative to the skin in any degree. Earlier medical tapes of heavy cloth backing construction had very limited extensibility so that when used upon portions of the anatomy subject to flexure, they either restricted such flexure or else moved relative to the skin during flexure, such relative movement taking place within the adhesive layer. This shearing of the adhesive caused transfer of adhesive mass to the skin resulting in considerable problems of removing the adhesive from the skin.

Modern medical tapes have improved adhesive and more extensible backings so that adhesive transfer to the skin is much less of a problem. The backings, while extensible, still require too much force to obtain a given degree of extension, so that they both restrict the movement of an anatomical joint and when the stress is removed, the tape is more elastic than the underlying skin causing the tape to no longer conform to the irregular topography of the skin.

Past efforts to design a conformable tape or dressing backing have concentrated largely upon using highly plasticized polymeric materials and rubbers or synthetic rubbers. Plasticized polymers, of which plasticized polyvinyl chloride is the most common example, have been used extensively for other types of tapes. The vinyl films usually contain 25 to 50% by weight plasticizer. With these tapes, there is tendency of the plasticizer to migrate into the pressure-sensitive adhesive layer, causing unpredictable changes in the properties of tape after prolonged storage.

Other prior art tapes have used rubber and synthetic rubbers, of which "Estane" thermoplastic polyurethane, as described in U.S. Pat. No. 3,483,018 (Waldman), is the most common example. These tapes also possess an undesirable amount of elasticity and strength.

To date, the prior art tapes have failed to duplicate the extensibility of the skin so that they are conformable during normal skin and joint flexure. Applicants have found a pressure-sensitive adhesive sheet material which is skin and joint conformable and extensible which comprises a backing sheet consisting essentially of chlorinated polyethylene and pressure-sensitive adhesive on at least a portion of at least one surface of the backing sheet.

More specifically the applicants have found a conformable adhesive sheet material comprising a backing sheet consisting essentially of chlorinated polyethylene and a pressure-sensitive adhesive on at least a portion of at least one surface of the backing sheet. The backing sheet requires less than about $25 \times 10^6$ dynes/cm$^2$ for an elongation of 20% as tested per ASTM Standard D-882 and has a stress relaxation with time when elongated 20% initially of from about 10% to about 20% after 1 minute and from about 20% to about 50% after 10 minutes.

The sheet material of the present invention closely matches the viscoelastic properties of skin. This backing sheet has been found to take less force to elongate than the skin and to have a relaxation rate more similar to skin than tapes of the prior art. This results in a more conformable tape that allows the skin to move naturally.

The invention may be better understood by reference to the attached drawing, wherein.

Figure 1:
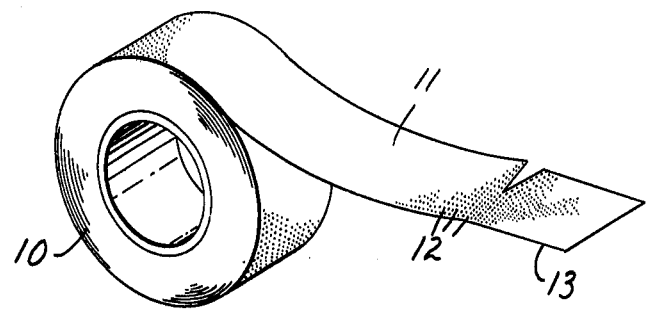
FIG. 1 is a roll of tape made in accordance with the present invention a portion of which has been unrolled and partially torn.

Referring to FIG. 1, a roll of tape 10, made in accordance with the present invention, is depicted with a portion unrolled. The tape is comprised of a backing sheet 11, a pressure-sensitive adhesive 13 on at least a portion of one surface of the backing sheet and perforations 12.

Figure 2:
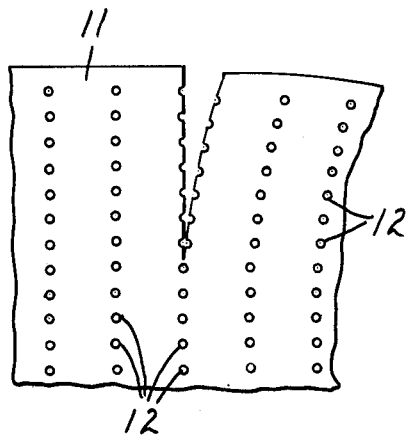
FIG. 2 is an enlarged view of a portion of the tape of FIG. 1 showing the relationship between the perforations.

The backing sheet 11 is a film which consists essentially of chlorinated polyethylene. Although FIGS. 1 and 2 depict a film, which is preferred, a backing of a non-woven web consisting essentially of chlorinated polyethylene fibers or a chlorinated polyethylene foam can be used in the present invention.

It is contemplated that the backing sheet of the present invention consists essentially of chlorinated polyethylene. It is preferably comprised of a blend of about 50 to about 100 percent by weight chlorinated polyethylene and from 0 to about 50 percent by weight polymeric extenders.

The preferred chlorinated polyethylene is a linear high density chlorinated polyethylene containing 35 to 55 percent by weight chlorine. This chlorinated polyethylene exhibits a 100% modulus (ASTM D-882) of from about 200 to 400 pounds per square inch. A preferred form of chlorinated polyethylene is Dow chlorinated polyethylene X02243.51, manufactured by Dow Chemical Co. of Midland, Mich.

As mentioned, polymeric extenders are preferably blended into the backing sheet. The polymeric extenders which are blended are those polymeric materials which have a higher modulus of elasticity than the chlorinated polyethylene used in the blend of the backing sheet. It has been found that the addition of higher modulus polymeric materials increases the backing sheets ability to resist deformation under the tensile stress. The increase in resistance to deformation contributes to the backing sheets ability to be unrolled when supplied in tape form. These higher modulus polymeric extenders are added only to the extent that the backing sheet requires less than about $25 \times 10^6$ dynes/cm$^2$ (approx. 360 p.s.i.) for an elongation of 20% (ASTM D-882). It has been found that including higher modulus polymeric material in the amount of about 10 to about 30 percent by weight of the blend yields such a property. Useful polymeric extenders include materials such as low density polyethylene, polypropylene, ethylene vinyl acetate, ethylene ethyl acrylate, isobutylene and polyvinyl chloride, with low density polyethylene in the amount of 16% by weight of the blend preferred.

It is also contemplated that other materials be added to the blend, e.g. chelating agents, internal lubricants, fillers, plasticizers, e.g. soybean oil, etc. in small amounts in order to improve the handling and process characteristics. Such materials normally do not detract from the desirable properties of the chlorinated polyethylene as long as the cumulative total of these materials and above mentioned extenders are present in less than 50% of the total composition. It has been found that as long as a chlorinated polyethylene is present in at least 50% by weight of the total composition, then the characteristic stretch properties of the process blend are those of chlorinated polyethylene.

The blend of which the backing sheet is comprised may be processed into the sheet material by numerous ways known to the art, e.g. extrusion, calendering, foaming, etc. It is preferred that calendering be used with the sheet material that is to be supplied in tape form. Extrusion sometimes results in a sheet material containing laminated layers within the film which separate along the interface when unrolled. Backing sheets of woven webs or foams are contemplated to be made utilizing standard techniques known to the art.

Conformability of the sheet material is to some degree related to the thickness and tensile strength of the backing sheet. It is preferred that the backing 11 be a thin film, web or foam of a higher tensile strength rather than being relatively thick and of a lower tensile strength. Skin has a tendency to wrinkle over anatomical joints when tension is removed from the joint. Thinner sheet material can more easily accommodate and conform to skin wrinkles. It is preferred that the thickness of the backing sheet when it is a film be in the range of 1.5 to 6.0 mils, or 0.038 to 0.152 mm.

It is well known that medical tapes should have a construction which permits a water vapor transmission, as tested per U.S. Federal Test Method Standard F-TMS-101B, 303, of at least 300 gm per square meter per twenty-four hours to prevent trauma or maceration of the underlying skin. Because the backing material of the present invention has a low water vapor permeability, the backing sheet 11, as shown in FIGS. 1 and 2 is preferably provided with closely spaced perforations 12 to provide satisfactory water vapor transmission. Such a perforated construction also provides for easy tearability. Perforation of the backing sheet 12 and the adhesive layer 13 being performed as disclosed in U.S. Pat. No. 3,085,024, Blackford, and U.S. Pat. No. 3,870,593, Elton.

Although less preferred, a backing sheet of a nonwoven web can be used which consists entirely of fibers consisting essentially of chlorinated polyethylene. Normally the fibers are bound by an elastic adhesive material that sizes and/or bonds the fibers.

The preferred adhesive 13 for the roll of tape 10 shown in FIGS. 1 and 2 is a porous or permeable medical grade adhesive, such as that disclosed in U.S. Pat. No. 3,121,027, Copeland which is applied to at least a portion of one surface of the film, foam or non-woven web.

It is contemplated that the sheet material be supplied and used both as rolls of tape 10, and also in the form of dressings as, for example, the well known first aid dressing wherein the tape has affixed to its adhesive surface an absorbent pad which can be applied over a wound. The sheet material can also be used as a surgical drape when supplied in sheet form with a release liner attached to the adhesive surface.

It has been found that when the tape is applied to the skin, both the underlying skin and the overlying adhesive tape are extended by the same forces acting upon the skin. Any force required to extend the tape must be applied to the tape by the skin. The present invention is therefore designed not to have stress-strain properties similar to that of skin as tapes of the prior art, but rather designed to have as low stress-strain properties as practical so that the strain imposed by tape against the skin is so insignificant as to be unnoticeable.

Elongation relaxation tests were run on human skin utilizing methods described in the book by R. M. Kenedi, T. Gibson and C. H. Daly "Structure and Function of Connective and Skeletal Tissue," London: Butterworths 1965 at page 388. It was found that when the skin was retained in a stressed condition, it exhibits a relaxation whereby the force required to maintain the same stress condition gradually declines. Test runs on tapes of the present invention in accordance with ASTM test D-882 indicate that for tapes to have elongation and relaxation similar to skin it must preferably exhibit a stress relaxation with time when elongated 20% of from about 10% to 20% after 1 minute and about 20% to about 50% after 10 minutes. The tapes of the present invention exhibit this stress relaxation with time and have sufficient relaxation properties to recover to near their original unstressed length when all stress is removed. This preferred range results in the elimination of the bothersome sagging of the tape and underlying skin.

Several specific examples of the invention are described below; however, it is understood that they are not to be construed to limit the invention. All parts are by weight unless specified otherwise.

EXAMPLE I

Dow chlorinated polyethylene X02243.51, commercially available from the Dow Chemical Co., of Midland, Mich., was blended in a Hobart model H-600T mixer (manufactured by the Hobart Co., of Troy, Ohio)

with: 0.5 part per hundred resin Vanstay SC (from Vanderbilt Co. of Norwalk, Conn.) a phosphite chelating agent; 2 parts per hundred resin of Paraplex G-62 an epoxidized soybean oil, commercially available from Rohm and Haas Co. of Chicago, Ill.; 20 parts per hundred resin of Microthene 710-20, a low density polyethylene, commercially available from USI Industrial Chemical Co., Division of National Distillers and Chemical Corp., New York, N.Y.; and 2 parts per hundred resin of calcium stearate. The resulting mixture was placed in a 300° F. (149° C.) Banbury, milled at 300° F. (149° C.) and calendered at 310° F. (154° C.) onto a carrier material (2-65 KG-1 silicone liner available from Daubert Coated Products Inc.) utilizing an inverted L. The resultant 4.5 mil (112.5 micrometers) thick film was allowed to cool and was tested according to ASTM Standards D-882. Results were as follows:

TABLE I

| ELONGATION | P.S.I. | FORCE DYNES/$cm^2 \times 10^6$ | LBS/IN WIDTH | DYNE/$cm \times 10^4$ |
|---|---|---|---|---|
| 2% | 33 | (2.275) | 0.15 | (2.626) |
| 5% | 56 | (3.860) | 0.25 | (4.378) |
| 10% | 89 | (6.136) | 0.40 | (7.004) |
| 20% | 133 | (9.169) | 0.60 | (10.507) |

Stress relaxation results were as follows at 20% elongation:

TABLE II

| TIME | P.S.I. | (D/$cm^2 \times 10^6$) | LBS/IN WIDTH | (D/cm $\times 10^4$) | DECREASE |
|---|---|---|---|---|---|
| 0 | 133 | 9.169 | 0.60 | 10.5071 | |
| 1 min | 111 | 7.652 | 0.50 | 8.7559 | 16.7% |
| 10 min | 89 | 6.136 | 0.40 | 7.0047 | 27% |

EXAMPLE II

Dow chlorinated polyethylene X02243.51, commercially available from the Dow Chemical Co. of Midland, Mich., was blended in a Hobart model H-600T mixer with: 0.5 part per hundred resin Vanstay SC" (from Vanderbilt Co. of Norwalk, Conn.) a phosphite chelating agent; 2 parts per hundred resin of Paraplex G-62 an epoxidized soybean oil, commercially available from Rohm and Haas Co. of Chicago, Ill.; 20 parts per hundred resin of Dow Polyethylene 510 high density polyethylene commercially available from the Dow Chemical Co. of Midland, Mich.; and 2 parts per hundred resin of calcium stearate. The resulting mixture was placed in a 300° F. (149° C.) Banbury, milled at 300° F. (149° C.) and calendered at a temperature of 310° F. (154° C.) onto a carrier material (2-65 KG-1 silicone liner available from Daubert Coated Product Inc.) utilizing an inverted L. The resultant 4 mil (100 micron) thickness film cooled and was tested according to ASTM Standards D-882. Results were as follows:

TABLE III

| ELONGATION | P.S.I. | FORCE $\frac{DYNES}{cm^2} \times 10^6$ | LBS/IN WIDTH | DYNES/cm $\times 10^4$ |
|---|---|---|---|---|
| 2% | 63 | 4.3435 | 0.25 | 4.3780 |
| 5% | 113 | 7.7907 | 0.45 | 7.8803 |
| 10% | 163 | 11.2380 | 0.65 | 11.3827 |
| 20% | 213 | 14.6852 | 0.85 | 14.8850 |

Stress-relaxation results were as follows at 20% elongation:

TABLE IV

| TIME | P.S.I. | $\frac{DYNES}{cm^2} \times 10^6$ | LBS/IN WIDTH | DYNES/ cm $\times 10^4$ | DECREASE |
|---|---|---|---|---|---|
| 0 | 213 | 14.6852 | 0.85 | 14.8850 | |
| 1 min | 188 | 12.9616 | 0.75 | 13.1339 | 12% |
| 10 min | 163 | 11.2380 | 0.65 | 11.3827 | 24% |

EXAMPLE III

An 80 lb. (135.6 g/m²) per ream silicone liner was coated with an acrylate adhesive as described in Copeland, U.S. Pat. No. 3,121,027 by a hopper knife. The liner was dried in a gas-fired forced air oven so the dry weight of adhesive was 10 grains per 24 sq. inches (41.86 gm/m²). A chlorinated polyethylene film made by the procedure outlined in Example II was laminated to the liner by running it through a pressure nip. The film on liner is coated with a low adhesion backsize of polyvinyl acetate-N-octadecyl carbamate. After drying in a gas-fired forced air oven the dry weight of the low adhesion backsize is 0.50 to 0.75 grain per 24 square inches (2.09 to 3.4 gm/m²). The film and liner is then run through the nip of an embossing roll and silicone rubber roll to provide perforations in the film and adhesive. The embossing roll is heated to 325° F. and the nip pressure is 60 to 80 pounds. The silicone liner is removed at slitting. The embossing facilitates tearing and the escape of moisture vapor. The resultant 6 mil (150 micron) tape was tested according to ASTM standard D-882. Results were as follows:

TABLE V

| ELONGATION | P.S.I. | DYNES/ $cm^2 \times 10^6$ | LBS/IN WIDTH | DYNES/ cm $\times 10^4$ |
|---|---|---|---|---|
| 2% | 42 | 2.8956 | 0.25 | 4.3780 |
| 5% | 83 | 5.72243 | 0.50 | 8.7559 |
| 10% | 125 | 8.61812 | 0.75 | 13.1339 |
| 20% | 158 | 10.8933 | 0.95 | 16.6362 |

TABLE VI

| TIME | P.S.I. | DYNES/ $cm^2 \times 10^6$ | LBS/IN WIDTH | DYNES cm $\times 10^4$ | DECREASE |
|---|---|---|---|---|---|
| 0 | 158 | 10.89331 | 0.95 | 16.6362 | |
| 1 min | 133 | 9.1698 | 0.80 | 14.0094 | 16% |
| 10 min | 100 | 6.8945 | 0.60 | 10.5071 | 37% |

EXAMPLES IV THROUGH VI

The following materials were compounded and processed as described in Example I:

| Example IV | Chlorinated Polyethylene | 100 parts |
| | Polyethylene | 30 parts |
| | Paraplex G-62 | 2 parts |
| | Vanstay SC | 0.5 parts |

|  |  | -continued |  |
|---|---|---|---|
|  | Calcium Stearate | 2 parts |  |
| Example V | Chlorinated Polyethylene | 100 parts |  |
|  | Polyethylene | 40 parts |  |
|  | Paraplex G-62 | 2 parts |  |
|  | Vanstay SC | 0.5 parts |  |
|  | Calcium Stearate | 2 parts |  |
| Example VI | Chlorinated Polyethylene | 100 parts |  |
|  | Polyethylene | 60 parts |  |
|  | Paraplex G-62 | 0 parts |  |
|  | Vanstay SC | 0.5 parts |  |
|  | Calcium Stearate | 2 parts |  |

The resultant 4.5 mil thick films were allowed to cool and were tested according to ASTM Standard D-882. Results were as follows:

TABLE VII

| | M.D. MODULUS | | | | | |
|---|---|---|---|---|---|---|
| | EXAMPLE IV | | EXAMPLE V | | EXAMPLE VI | |
| % ELONGATION | PSI | DYNES/ $cm^2 \times 10^6$ | PSI | DYNES/ $cm^2 \times 10^6$ | PSI | DYNES/ $cm^2 \times 10^6$ |
| 2 | 62.5 | 4.3101 | 67.5 | 4.6549 | 75 | 5.1721 |
| 5 | 117.5 | 8.1029 | 130 | 8.9649 | 190 | 13.1026 |
| 10 | 185 | 12.7578 | 220 | 15.1714 | 270 | 18.6195 |
| 20 | 260 | 17.9299 | 312.5 | 21.5503 | 345 | 23.7915 |
| Break | 1360 | 93.7870 | 1122.5 | 77.4087 | 740 | 51.0311 |
|  | (720% E) |  | (410% E) |  | (340% E) |  |

TABLE VIII

| | C.D. MODULUS | | | | | |
|---|---|---|---|---|---|---|
| | EXAMPLE IV | | EXAMPLE V | | EXAMPLE VI | |
| % Elongation | PSI | DYNES/ $cm^2 \times 10^6$ | PSI | DYNES/ $cm^2 \times 10^6$ | PSI | DYNES/ $cm^2 \times 10^6$ |
| 2 | 55 | 3.7929 | 40 | 2.7584 | 62.5 | 4.3100 |
| 5 | 107.5 | 7.4133 | 100 | 6.8961 | 137.5 | 9.4821 |
| 10 | 165 | 11.3786 | 177.5 | 12.2406 | 247.5 | 17.0678 |
| 20 | 225 | 15.5162 | 245 | 16.8954 | 337.5 | 23.2743 |
| Break | 1032.5 | 71.2022 | 645 | 44.4798 | 482.5 | 33.2737 |
|  | (640% E) |  | (380% E) |  | (170% E) |  |

TABLE IX

| | M.D. STRESS RELAXATION | | | | | | | |
|---|---|---|---|---|---|---|---|---|
| | EXAMPLE IV | | | EXAMPLE V | | | EXAMPLE VI | |
| Time Min | PSI | Dynes/ $cm^2 \times 10^6$ | % Decrease | PSI | Dynes/ $cm^2 \times 10^6$ | % Decrease | PSI | Dynes/ $cm^2 \times 10^6$ | % Decrease |
| 0 | 260 | 17.9299 |  | 312.5 | 21.5503 |  | 345 | 23.7915 |  |
| 1 | 226 | 15.5852 | 13.1 | 279 | 19.2401 | 10.7 | 310 | 21.3779 | 10.2 |
| 10 | 197 | 13.5853 | 24.3 | 243 | 16.7575 | 22.3 | 278 | 19.1712 | 19.5 |

What is claimed is:

1. A conformable adhesive sheet material having viscoelastic properties similar to human skin comprising a backing sheet consisting essentially of chlorinated polyethylene and a pressure sensitive adhesive on at least a portion of at least one surface of said backing sheet, said backing sheet requiring less than about $25 \times 10^6$ dynes/cm$^2$ for an elongation of 20% as tested per ASTM Standard D-882 and having a stress relaxation with time when elongated 20% initially of from about 10% to about 20% after 1 minute and from about 20% to about 50% after 10 minutes.

2. The conformable adhesive sheet material of claim 1 wherein said backing sheet consists essentially of a blend consisting essentially of from about 50 to 100 percent by weight chlorinated polyethylene and from about 0 to about 50 percent by weight polymeric extender having a higher modulus of elasticity than chlorinated polyethylene.

3. The conformable adhesive sheet material of claim 2 wherein said backing sheet is a non-woven web of fibers consisting essentially of chlorinated polyethylene.

4. The conformable adhesive sheet material of claim 2 wherein said backing sheet consists essentially of from about 10% to 30% by weight of said polymeric extender.

5. The conformable adhesive sheet material of claim 1 wherein said backing sheet is foam.

6. The conformable sheet material of claim 1 wherein said backing sheet is a film.

7. The conformable sheet material of claim 1 wherein said sheet material is provided with perforations.

8. A conformable adhesive surgical drape having viscoelastic properties similar to human skin comprising a backing sheet consisting essentially of chlorinated polyethylene, a pressure sensitive adhesive on at least a portion of at least one surface of said backing sheet, and a release liner covering said adhesive, said backing sheet requiring less than about $25 \times 10^6$ dynes/cm$^2$ for an elongation of 20% as tested per ASTM Standard D-882 and having a stress relaxation with time when elongated 20% initially of from about 10% to about 20% after 1 minute and from about 20% to about 50% after 10 minutes.

* * * * *